United States Patent
Watanabe et al.

(10) Patent No.: US 12,066,396 B2
(45) Date of Patent: Aug. 20, 2024

(54) SENSOR ELEMENT

(71) Applicant: NGK INSULATORS, LTD., Nagoya (JP)

(72) Inventors: Yusuke Watanabe, Nagoya (JP); Kengo Terasawa, Nagoya (JP); Shiho Iwai, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 103 days.

(21) Appl. No.: 17/189,295

(22) Filed: Mar. 2, 2021

(65) Prior Publication Data

US 2021/0302362 A1 Sep. 30, 2021

(30) Foreign Application Priority Data

Mar. 25, 2020 (JP) ................................. 2020-054413

(51) Int. Cl.
*G01N 27/41* (2006.01)
*G01N 27/407* (2006.01)

(52) U.S. Cl.
CPC ......... *G01N 27/41* (2013.01); *G01N 27/4076* (2013.01)

(58) Field of Classification Search
CPC ............... G01N 27/41; G01N 27/4076; G01N 33/0037; G01N 27/417; G01N 27/26
See application file for complete search history.

(56) References Cited

U.S. PATENT DOCUMENTS

| | | | |
|---|---|---|---|
| 4,294,668 A | 10/1981 | Young | |
| 5,763,763 A | 6/1998 | Kato et al. | |
| 2003/0136674 A1* | 7/2003 | Kato | G01N 27/419 204/431 |
| 2003/0201171 A1* | 10/2003 | Nakagaki | G01N 27/419 204/290.01 |
| 2004/0188251 A1* | 9/2004 | Kurachi | G01N 27/419 204/426 |

(Continued)

FOREIGN PATENT DOCUMENTS

| | | |
|---|---|---|
| JP | S55-39096 A | 3/1980 |
| JP | 2000-28576 A | 1/2000 |

(Continued)

OTHER PUBLICATIONS

Japanese Office Action received in corresponding Japanese Application No. 2020-054413 dated Jul. 4, 2023.

*Primary Examiner* — Luan V Van
*Assistant Examiner* — Shizhi Qian
(74) *Attorney, Agent, or Firm* — MATTINGLY & MALUR, PC

(57) ABSTRACT

In a sensor element for a limiting-current type gas sensor measuring concentration of NOx in a measurement gas, an inner pump electrode located to face a first internal space communicating with a gas inlet through which the measurement gas is introduced from an external space under predetermined diffusion resistance is made of a cermet of a Pt—Au alloy and zirconia, and the inner pump electrode is located, from among surfaces defining the first internal space, at least on a surface farthest from a heater part in a thickness direction of the element, and is not located on a surface closest to the heater part in the thickness direction.

12 Claims, 8 Drawing Sheets

(56) References Cited

U.S. PATENT DOCUMENTS

| | | | |
|---|---|---|---|
| 2007/0119708 A1* | 5/2007 | Oya | G01N 27/4175 |
| | | | 205/775 |
| 2011/0036715 A1* | 2/2011 | Horisaka | G01N 27/419 |
| | | | 204/424 |
| 2016/0258897 A1* | 9/2016 | Sakakibara | G01N 27/419 |
| 2017/0276636 A1* | 9/2017 | Tominaga | G01N 27/4067 |
| 2019/0120791 A1* | 4/2019 | Al-Gouhi | G01N 27/44769 |
| 2019/0242404 A1* | 8/2019 | Whitmire | F21V 33/0092 |

FOREIGN PATENT DOCUMENTS

| | | |
|---|---|---|
| JP | 3050781 B2 | 3/2000 |
| JP | 2014-190940 A | 10/2014 |
| JP | 2014-209128 A | 11/2014 |

* cited by examiner

F I G. 6
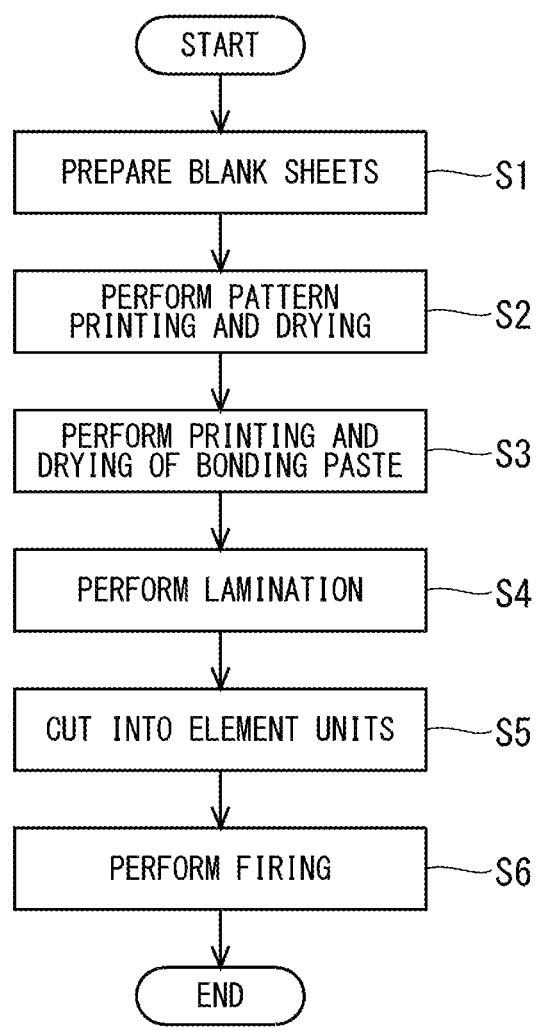

SENSOR ELEMENT

CROSS-REFERENCE TO RELATED APPLICATION

The present application claims priority from Japanese application JP2020-054413, filed on Mar. 25, 2020, the contents of which is hereby incorporated by reference into this application.

BACKGROUND OF THE INVENTION

Field of the Invention

The present invention relates to a gas sensor for determining the concentration of nitrogen oxides (NOx), and, in particular, to suppression of deterioration of measurement sensitivity of a sensor element thereof.

Description of the Background Art

A limiting-current type gas sensor (NOx sensor) including a sensor element containing an oxygen-ion conductive solid electrolyte as a main component has already been known (see, for example, Japanese Patent No. 3050781). In determining a NOx concentration using such a gas sensor, a measurement gas is first introduced into a space (an internal space) inside the sensor element under predetermined diffusion resistance, and oxygen in the measurement gas is pumped out by an electrochemical pump cell, for example, referred to as a main pump cell and an auxiliary pump cell (a first electrochemical pump cell and a second electrochemical pump cell in Japanese Patent No. 3050781) to sufficiently reduce an oxygen concentration of the measurement gas in advance. NOx in the measurement gas is then reduced or decomposed by a measurement electrode (third inner pump electrode in Japanese Patent No. 3050781) functioning as a reduction catalyst, and oxygen thus generated is pumped out by an electrochemical pump cell (a third electrochemical pump cell in Japanese Patent No. 3050781) different from the above-mentioned electrochemical pump cell, including the measurement electrode, and, for example, referred to as a measurement pump cell. The NOx concentration is determined using a constant functional relationship between a current (NOx current) flowing through the measurement pump cell and the NOx concentration.

In the gas sensor (NOx sensor), use of Pt to which Au has been added (an Au—Pt alloy) as a metal component of an inner pump electrode located in the internal space and forming the main pump cell in order to suppress decomposition of NOx caused when the main pump cell pumps out oxygen from the internal space and to enhance NOx detection accuracy has already been known (see, for example, Japanese Patent Application Laid-Open No. 2014-190940 and Japanese Patent Application Laid-Open No. 2014-209128).

A gas sensor as disclosed in Japanese Patent No. 3050781, Japanese Patent Application Laid-Open No. 2014-190940, and Japanese Patent Application Laid-Open No. 2014-209128 is used in a state of being heated to a high temperature to activate a solid electrolyte, so that, if the measurement gas having a high oxygen concentration continues to be introduced into the internal space, $PtO_2$ generated through oxidation of Pt in the pump electrode located in the space may evaporate (transpire), and, furthermore, Au might evaporate (transpire) together. Such evaporation of Au causes a problem in that NOx is decomposed before the measurement gas reaches the measurement electrode thereby to deteriorate measurement accuracy (measurement sensitivity). Attachment of evaporating Au to the measurement electrode causes deterioration of the measurement accuracy and deterioration of responsiveness.

SUMMARY

The present invention relates to a gas sensor for determining the concentration of nitrogen oxides (NOx), and is, in particular, directed to a configuration to suppress deterioration of measurement sensitivity of a sensor element thereof.

According to the present invention, a sensor element for a limiting-current type gas sensor measuring concentration of NOx in a measurement gas having a base part made of an oxygen-ion conductive solid electrolyte includes: a gas inlet through which the measurement gas is introduced from an external space; a first internal space communicating with the gas inlet under predetermined diffusion resistance; a main pump cell as an electrochemical pump cell including an inner pump electrode located to face the first internal space, an out-of-space pump electrode located to face a space other than the first internal space, and the solid electrolyte located between the inner pump electrode and the out-of-space pump electrode; a measurement electrode located inside the sensor element, at least one diffusion control part being located between the measurement electrode and the first internal space; a reference electrode located inside the sensor element and capable of being in contact with a reference gas; a measurement pump cell as an electrochemical pump cell including the measurement electrode, the out-of-space pump electrode, and the solid electrolyte located between the measurement electrode and the out-of-space pump electrode; and a heater part buried in the sensor element and heating the sensor element. The inner pump electrode is at least made of a cermet of a Pt—Au alloy and zirconia, and the inner pump electrode is located, from among surfaces defining the first internal space, at least on a surface farthest from the heater part in a thickness direction of the sensor element, and is not located on a surface closest to the heater part in the thickness direction, or the inner pump electrode is not located between the heater part and the first internal space at least in a thickness direction of the sensor element.

In the sensor element, the inner pump electrode is not disposed at a location where Au is likely to evaporate due to heating of the sensor element by the heater part when the gas sensor is in use, thereby to reduce the influence of evaporation of Au from the inner pump electrode on NOx sensitivity, so that the gas sensor in which deterioration of the NOx sensitivity over time is suppressed even in a case where the gas sensor is in continuous use is achieved.

A current flowing through the main pump cell when the sensor element is driven under a gas atmosphere having an oxygen concentration of 18% and the balance being nitrogen preferably has a current density of 0.4 $mA/mm^2$ or less.

In this case, an excessive increase in main pump voltage applied to the main pump cell to cause decomposition of NOx in a case where the oxygen concentration is high is suppressed.

The sensor element may further include another diffusion control part composed of a pair of slits communicating with the first internal space, and located between the gas inlet and the first internal space. Diffusion resistance is set to higher at a first slit of the pair of slits farther from the heater part in the thickness direction than at a second slit of the pair of slits closer to the heater part in the thickness direction.

In this case, pumping out of oxygen in the inner pump electrode is leveled, and application of a locally high main pump voltage between a region of the inner pump electrode closer to the diffusion control part and the out-of-space pump electrode to cause decomposition of NOx is desirably suppressed.

It is thus an object of the present invention to provide a gas sensor in which deterioration of measurement sensitivity with use over time is suppressed.

These and other objects, features, aspects and advantages of the present invention will become more apparent from the following detailed description of the present invention when taken in conjunction with the accompanying drawings.

BRIEF DESCRIPTION OF THE DRAWINGS

FIG. 6 is a flowchart showing processing when the sensor element 101 is manufactured;

DESCRIPTION OF THE PREFERRED EMBODIMENTS

<General Configuration of Gas Sensor>

A general configuration of a gas sensor 100 including a sensor element 101 according to the present embodiment will be described first. In the present embodiment, the gas sensor 100 is a limiting-current type NOx sensor sensing NOx and measuring the concentration thereof using the sensor element 101. The gas sensor 100 further includes a controller 110 controlling operation of each part and identifying the NOx concentration based on a NOx current flowing through the sensor element 101.

Figure 1:
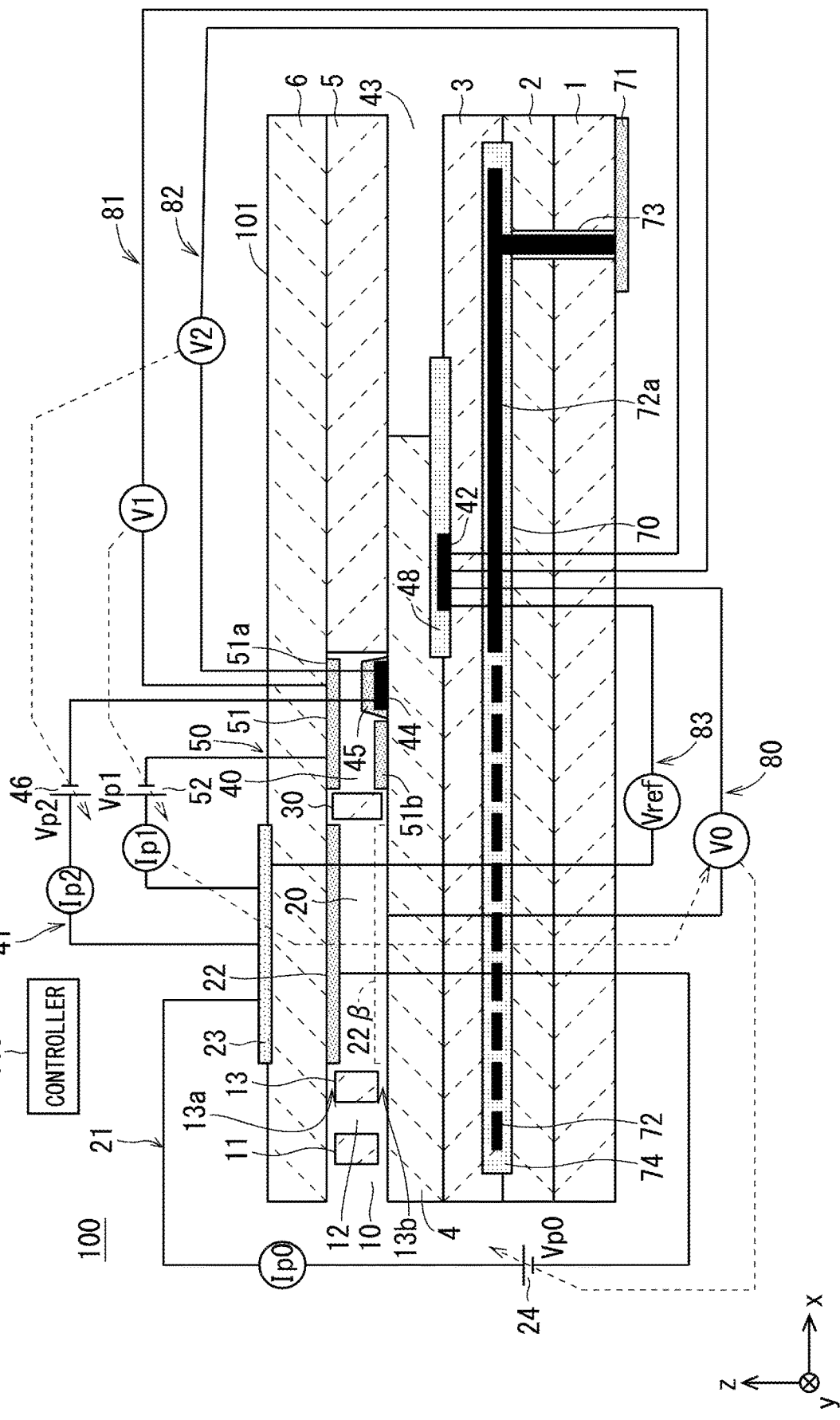
FIG. 1 schematically shows one example of a configuration of a gas sensor 100 including a vertical sectional view taken along a longitudinal direction of a sensor element 101.

FIG. 1 schematically shows one example of a configuration of the gas sensor 100 including a vertical sectional view taken along a longitudinal direction of the sensor element 101. A right-handed xyz coordinate having the longitudinal direction, a width direction, and a thickness direction of the sensor element 101 respectively as an x-axis direction, a y-axis direction, and a z-axis direction has been attached to FIG. 1 (the same applies to FIGS. 2A, 2B, 3, 4A, 4B, 5, and 7).

The sensor element 101 is a planar (elongated planar) element having a structure in which six solid electrolyte layers, namely, a first substrate layer 1, a second substrate layer 2, a third substrate layer 3, a first solid electrolyte layer 4, a spacer layer 5, and a second solid electrolyte layer 6 each made of zirconia ($ZrO_2$) (e.g., yttria stabilized zirconia (YSZ)) as an oxygen-ion conductive solid electrolyte are laminated in the stated order from a bottom side of FIG. 1. The solid electrolyte forming these six layers is dense and airtight. A surface on an upper side (a positive side in the z-axis direction) and a surface on a lower side (a negative side in the z-axis direction) of each of these six layers in FIG. 1 are hereinafter also simply referred to as an upper surface and a lower surface, respectively. A part of the sensor element 101 made of the solid electrolyte as a whole is generically referred to as a base part.

The sensor element 101 is manufactured, for example, by performing predetermined processing, printing of circuit patterns, and the like on ceramic green sheets corresponding to the respective layers, then laminating them, and further firing them for integration.

Between a lower surface of the second solid electrolyte layer 6 and an upper surface of the first solid electrolyte layer 4 in one leading end portion (on a negative side in the x-axis direction) of the sensor element 101, a gas inlet 10, a first diffusion control part 11, a buffer space 12, a second diffusion control part 13, a first internal space 20, a third diffusion control part 30, and a second internal space 40 are formed adjacent to each other to communicate in the stated order.

The gas inlet 10, the buffer space 12, the first internal space 20, and the second internal space 40 are spaces inside the sensor element 101 provided to penetrate the spacer layer 5, having an upper portion and a lower portion respectively defined by the lower surface of the second solid electrolyte layer 6 and the upper surface of the first solid electrolyte layer 4, and having a side portion surrounded by the spacer layer 5.

The first diffusion control part 11, the second diffusion control part 13, and the third diffusion control part 30 are each provided as two horizontally long slits (whose openings have longitudinal directions perpendicular to the page of FIG. 1). A part extending from the gas inlet 10 to the second internal space 40 is also referred to as a gas distribution part.

At a location farther from the leading end than the gas distribution part is, a reference gas introduction space 43 having a side portion defined by a side surface of the first solid electrolyte layer 4 is provided between an upper surface of the third substrate layer 3 and a lower surface of the spacer layer 5. For example, air is introduced into the reference gas introduction space 43 as a reference gas when the NOx concentration is measured.

An air introduction layer 48 is a layer made of porous alumina, and the reference gas is introduced into the air introduction layer 48 through the reference gas introduction space 43. The air introduction layer 48 is formed to cover a reference electrode 42.

The reference electrode 42 is an electrode formed to be sandwiched between the upper surface of the third substrate layer 3 and the first solid electrolyte layer 4, and the air introduction layer 48 leading to the reference gas introduction space 43 is provided around the reference electrode 42 as described above. As will be described below, an oxygen concentration (oxygen partial pressure) in the first internal space 20 and the second internal space 40 can be measured using the reference electrode 42.

In the gas distribution part, the gas inlet 10 is a part opening to an external space, and a measurement gas is taken from the external space into the sensor element 101 through the gas inlet 10.

The first diffusion control part 11 is a part providing predetermined diffusion resistance to the measurement gas taken through the gas inlet 10.

The buffer space 12 is a space provided to guide the measurement gas introduced through the first diffusion control part 11 to the second diffusion control part 13.

The second diffusion control part 13 is a part providing predetermined diffusion resistance to the measurement gas introduced from the buffer space 12 into the first internal space 20. From among the two slits constituting the second diffusion control part 13, a slit on an upper side (the positive side in the z-axis direction) in FIG. 1 is, in particular, referred to as an upper slit 13a, and a slit on a lower side (the negative side in the z-axis direction) in FIG. 1 is, in particular, referred to as a lower slit 13b.

In introducing the measurement gas from outside the sensor element 101 into the first internal space 20, the measurement gas having abruptly been taken into the sensor element 101 through the gas inlet 10 due to pressure fluctuations (pulsation of exhaust pressure in a case where the measurement gas is an exhaust gas of a vehicle) of the measurement gas in the external space is not directly introduced into the first internal space 20 but is introduced into the first internal space 20 after concentration fluctuations of the measurement gas are canceled through the first diffusion control part 11, the buffer space 12, and the second diffusion control part 13. This makes the concentration fluctuations of the measurement gas introduced into the first internal space 20 almost negligible.

The first internal space 20 is provided as a space to adjust oxygen partial pressure of the measurement gas introduced through the second diffusion control part 13. The oxygen partial pressure is adjusted by operating a main pump cell 21.

The main pump cell 21 is an electrochemical pump cell including an inner pump electrode 22, an outer (out-of-space) pump electrode 23, and the second solid electrolyte layer 6 sandwiched between these electrodes. The inner pump electrode 22 is provided on substantially the entire lower surface of a portion of the second solid electrolyte layer 6 facing the first internal space 20, and the outer pump electrode 23 is provided in a region, on an upper surface of the second solid electrolyte layer 6 (one main surface of the sensor element 101), corresponding to the inner pump electrode 22 to be exposed to the external space.

The inner pump electrode 22 is provided on the lower surface of the second solid electrolyte layer 6 as a ceiling surface of the first internal space 20 to be rectangular in plan view. FIG. 1 illustrates a case where the inner pump electrode 22 is provided over substantially the entire range on the lower surface of the portion of the second solid electrolyte layer 6 in the longitudinal direction of the element, but this is just an example. The inner pump electrode 22 is formed using a material having a weakened reducing ability with respect to a NOx component in the measurement gas. Specifically, the inner pump electrode 22 is formed as a porous cermet electrode of an Au—Pt alloy and $ZrO_2$. Containment (addition) of Au has an effect of weakening the reducing ability with respect to the NOx component. Details of the inner pump electrode 22 will be described below.

On the other hand, the outer pump electrode 23 is formed, for example, as a porous cermet electrode of Pt or an alloy thereof and $ZrO_2$ to be rectangular in plan view.

The main pump cell 21 can pump out oxygen in the first internal space 20 to the external space or pump in oxygen in the external space to the first internal space 20 by applying, from a variable power supply 24, a desired pump voltage Vp0 between the inner pump electrode 22 and the outer pump electrode 23 to allow a main pump current Ip0 to flow between the inner pump electrode 22 and the outer pump electrode 23 in a positive or negative direction. The pump voltage Vp0 applied between the inner pump electrode 22 and the outer pump electrode 23 by the main pump cell 21 is also referred to as a main pump voltage Vp0.

To detect the oxygen concentration (oxygen partial pressure) in an atmosphere in the first internal space 20, the inner pump electrode 22, the second solid electrolyte layer 6, the spacer layer 5, the first solid electrolyte layer 4, the third substrate layer 3, and the reference electrode 42 constitute a main sensor cell 80 as an electrochemical sensor cell.

The oxygen concentration (oxygen partial pressure) in the first internal space 20 can be known by measuring electromotive force V0 in the main sensor cell 80.

Furthermore, the controller 110 performs feedback control of the main pump voltage Vp0 so that the electromotive force V0 is constant, thereby to control the main pump current Ip0. The oxygen concentration in the first internal space 20 is thereby maintained to have a predetermined constant value.

The third diffusion control part 30 is a part providing predetermined diffusion resistance to the measurement gas having an oxygen concentration (oxygen partial pressure) controlled by operation of the main pump cell 21 in the first internal space 20, and guiding the measurement gas to the second internal space 40.

The second internal space 40 is provided as a space to perform processing concerning measurement of the nitrogen oxide (NOx) concentration of the measurement gas introduced through the third diffusion control part 30. The NOx concentration is measured, mainly in the second internal space 40 in which the oxygen concentration has been adjusted by an auxiliary pump cell 50, further by operation of a measurement pump cell 41.

After the oxygen concentration (oxygen partial pressure) is adjusted in advance in the first internal space 20, the auxiliary pump cell 50 further adjusts the oxygen partial pressure of the measurement gas introduced through the third diffusion control part 30 in the second internal space 40. The oxygen concentration in the second internal space 40 can thereby be maintained constant with high accuracy, and thus the NOx concentration can be measured with high accuracy in the gas sensor 100.

The auxiliary pump cell 50 is an auxiliary electrochemical pump cell including an auxiliary pump electrode 51, the outer pump electrode 23 (not limited to the outer pump electrode 23 and only required to be any appropriate electrode outside the sensor element 101), and the second solid electrolyte layer 6. The auxiliary pump electrode 51 has a ceiling electrode portion 51a provided on substantially the entire lower surface of a portion of the second solid electrolyte layer 6 facing the second internal space 40.

The auxiliary pump electrode 51 is formed on upper and lower solid electrolyte layers (the second solid electrolyte layer 6 and the first solid electrolyte layer 4) defining the second internal space 40. Specifically, the ceiling electrode portion 51a is formed on the lower surface of the second solid electrolyte layer 6 as a ceiling surface of the second internal space 40, and a bottom electrode portion 51b is formed on the upper surface of the first solid electrolyte layer 4 as a bottom surface of the second internal space 40.

The ceiling electrode portion 51a and the bottom electrode portion 51b are rectangular in plan view, and are connected by a conducting portion (not illustrated) provided on the side wall surface (inner surface) of the spacer layer 5 forming opposite side wall portions of the second internal space 40.

As with the inner pump electrode 22, the auxiliary pump electrode 51 is formed using a material having a weakened reducing ability with respect to the NOx component in the measurement gas. The auxiliary pump electrode 51 is formed, for example, as a cermet electrode of an Au—Pt alloy containing Au of approximately 0.6 wt % to 1.4 wt % and $ZrO_2$ to have a porosity of 5% to 40% and a thickness of 5 μm to 20 μm. The Au—Pt alloy and $ZrO_2$ are only required to have a weight ratio Pt:$ZrO_2$ of approximately 7.0:3.0 to 5.0:5.0.

The auxiliary pump cell 50 can pump out oxygen in an atmosphere in the second internal space 40 to the external space or pump in oxygen in the external space to the second internal space 40 by applying a desired voltage Vp1 between the auxiliary pump electrode 51 and the outer pump electrode 23 under control performed by the controller 110.

To control the oxygen partial pressure in the atmosphere in the second internal space 40, the auxiliary pump electrode 51, the reference electrode 42, the second solid electrolyte layer 6, the spacer layer 5, the first solid electrolyte layer 4, and the third substrate layer 3 constitute an auxiliary sensor cell 81 as an electrochemical sensor cell.

The auxiliary pump cell 50 performs pumping using a variable power supply 52 whose voltage is controlled based on electromotive force V1 detected in the auxiliary sensor cell 81 in accordance with the oxygen partial pressure in the second internal space 40. The oxygen partial pressure in the atmosphere in the second internal space 40 is thereby controlled to a low partial pressure having substantially no effect on measurement of NOx.

At the same time, a resulting auxiliary pump current Ip1 is used to control the electromotive force in the main sensor cell 80. Specifically, the auxiliary pump current Ip1 is input, as a control signal, into the main sensor cell 80, and, through control of the electromotive force V0 therein, the oxygen partial pressure of the measurement gas introduced through the third diffusion control part 30 into the second internal space 40 is controlled to have a gradient that is always constant. In use as the NOx sensor, the oxygen concentration in the second internal space 40 is maintained to have a constant value of approximately 0.001 ppm by the action of the main pump cell 21 and the auxiliary pump cell 50.

The measurement pump cell 41 measures the NOx concentration of the measurement gas in the second internal space 40. The measurement pump cell 41 is an electrochemical pump cell including a measurement electrode 44, the outer pump electrode 23, the second solid electrolyte layer 6, the spacer layer 5, and the first solid electrolyte layer 4. The measurement electrode 44 is provided on an upper surface of a portion of the first solid electrolyte layer 4 facing the second internal space 40 to be separated from the third diffusion control part 30.

The measurement electrode 44 is a porous cermet electrode. The measurement electrode 44 is formed, for example, as a cermet electrode of Pt or an alloy thereof and $ZrO_2$. The measurement electrode 44 also functions as a NOx reduction catalyst to reduce NOx existing in the atmosphere in the second internal space 40. Furthermore, the measurement electrode 44 is covered with a fourth diffusion control part 45.

The fourth diffusion control part 45 is a film formed of a porous body containing alumina ($Al_2O_3$) as a main component. The fourth diffusion control part 45 plays a role in limiting the amount of NOx flowing into the measurement electrode 44, and also functions as a protective film of the measurement electrode 44.

The measurement pump cell 41 can pump out oxygen generated through decomposition of NOx in an atmosphere around the measurement electrode 44, and detect the amount of generated oxygen as a pump current Ip2 under control performed by the controller 110.

To detect the oxygen partial pressure around the measurement electrode 44, the second solid electrolyte layer 6, the spacer layer 5, the first solid electrolyte layer 4, the third substrate layer 3, the measurement electrode 44, and the reference electrode 42 constitute a measurement sensor cell 82 as an electrochemical sensor cell. A variable power supply 46 is controlled based on electromotive force V2 detected in the measurement sensor cell 82 in accordance with the oxygen partial pressure around the measurement electrode 44.

The measurement gas introduced into the second internal space 40 is to reach the measurement electrode 44 through the fourth diffusion control part 45 under a situation in which the oxygen partial pressure is controlled. NOx in the measurement gas around the measurement electrode 44 is reduced ($2NO \rightarrow N_2 + O_2$) to generate oxygen. Oxygen as generated is to be pumped by the measurement pump cell 41, and, at this time, a voltage Vp2 of the variable power supply 46 is controlled so that the electromotive force V2 detected in the measurement sensor cell 82 is constant. The amount of oxygen generated around the measurement electrode 44 is proportional to the NOx concentration of the measurement gas, and thus the NOx concentration of the measurement gas is to be calculated using the pump current Ip2 in the measurement pump cell 41. The pump current Ip2 is hereinafter also referred to as a NOx current Ip2.

If the measurement electrode 44, the first solid electrolyte layer 4, the third substrate layer 3, and the reference electrode 42 are combined to constitute an oxygen partial pressure detection means as an electrochemical sensor cell, electromotive force in accordance with a difference between the amount of oxygen generated through reduction of a NOx component in the atmosphere around the measurement electrode 44 and the amount of oxygen contained in reference air can be detected, and the concentration of the NOx component in the measurement gas can thereby be determined.

The second solid electrolyte layer 6, the spacer layer 5, the first solid electrolyte layer 4, the third substrate layer 3, the outer pump electrode 23, and the reference electrode 42 constitute an electrochemical sensor cell 83, and oxygen partial pressure of the measurement gas outside the sensor can be detected using electromotive force Vref obtained by the sensor cell 83.

The sensor element 101 further includes a heater part 70 playing a role in temperature adjustment of heating the sensor element 101 and maintaining the temperature thereof to enhance oxygen ion conductivity of the solid electrolyte forming the base part.

The heater part 70 mainly includes a heater electrode 71, a heater element 72, a heater lead 72a, a through hole 73, and a heater insulating layer 74. A portion of the heater part 70 other than the heater electrode 71 is buried in the base part of the sensor element 101.

The heater electrode 71 is an electrode formed to be in contact with a lower surface of the first substrate layer 1 (the other main surface of the sensor element 101).

The heater element 72 is a resistive heating element provided between the second substrate layer 2 and the third substrate layer 3. The heater element 72 generates heat by being powered from a heater power supply, which is not illustrated in FIG. 1, outside the sensor element 101 through the heater electrode 71, the through hole 73, and the heater lead 72a, which constitute a current-carrying path. The heater element 72 is made of Pt, or contains Pt as a main component. The heater element 72 is buried, in a predetermined range of the sensor element 101 in which the gas distribution part is provided, to oppose the gas distribution part in the thickness direction of the element. The heater element 72 is provided to have a thickness of approximately 10 μm to 20 μm.

In the sensor element 101, each part of the sensor element 101 can be heated to a predetermined temperature and the temperature can be maintained by allowing a current to flow through the heater electrode 71 to the heater element 72 to thereby cause the heater element 72 to generate heat. Specifically, the sensor element 101 is heated so that the solid electrolyte and the electrodes in the vicinity of the gas distribution part are at a temperature of approximately 700° C. to 900° C. The oxygen ion conductivity of the solid electrolyte forming the base part in the sensor element 101 is enhanced by the heating. A heating temperature of the heater element 72 when the gas sensor 100 is in use (when the sensor element 101 is driven) is referred to as a sensor element driving temperature.

In the gas sensor 100 having a configuration as described above, oxygen contained in the measurement gas is pumped out by operating the main pump cell 21 and further the auxiliary pump cell 50, and the measurement gas having oxygen partial pressure sufficiently reduced to a degree (e.g., 0.0001 ppm to 1 ppm) having substantially no effect on measurement of NOx reaches the measurement electrode 44. NOx in the measurement gas having reached the measurement electrode 44 is reduced to generate oxygen. Oxygen as generated is pumped out by the measurement pump cell 41, and the NOx current Ip2 flowing at the pumping out and the concentration of NOx in the measurement gas have a constant functional relationship (hereinafter, referred to as sensitivity characteristics).

The sensitivity characteristics are identified in advance using a plurality of types of model gases having known NOx concentrations prior to actual use of the gas sensor 100, and data thereof is stored in the controller 110. In actual use of the gas sensor 100, a signal representing a value of the NOx current Ip2 flowing in accordance with the NOx concentration of the measurement gas is momentarily provided to the controller 110, and the controller 110 successively calculates and outputs NOx concentrations based on the value and the identified sensitivity characteristics. The NOx concentration of the measurement gas can thereby be known in almost real time using the gas sensor 100.

<Details of Inner Pump Electrode and Main Pump Cell Current Density>

The inner pump electrode 22 provided to face the first internal space 20 will be described in more detail next.

As described above, the inner pump electrode 22 is provided on the lower surface of the second solid electrolyte layer 6 to be rectangular in plan view and to have a thickness of approximately 5 μm to 20 μm. A weight ratio of the Au—Pt alloy and $ZrO_2$ of the inner pump electrode 22 is only required to approximately be Pt:$ZrO_2$ of 7.0:3.0 to 5.0:5.0.

In contrast to the auxiliary pump electrode 51, however, the inner pump electrode 22 is not provided in a region, such as a region 22β shown in a broken line in FIG. 1, on the upper surface of the first solid electrolyte layer 4 defining the first internal space 20. This takes into account that the region 22β is closer to the heater part 70 than a location of formation of the inner pump electrode 22 is, and thus is heated by the heater part 70 to a higher temperature than the location of formation of the inner pump electrode 22 when the gas sensor 100 is in use. In a case where the element driving temperature is set to 850° C. in the sensor element 101 in which the height of the first internal space 20 (the thickness of the spacer layer 5) is approximately 50 μm to 400 μm, for example, a temperature difference of approximately 20° ° C. to 80° C. can occur between the lower surface of the second solid electrolyte layer 6 on which the inner pump electrode 22 is disposed and the upper surface of the first solid electrolyte layer 4 on which the inner pump electrode 22 is not disposed.

In other words, the inner pump electrode 22 is provided, from among surfaces defining the first internal space 20, only on a surface farthest from the heater part 70 in the thickness direction of the element (the z-axis direction), and is not provided on a surface closest to the heater part 70 opposing the farthest surface. That is, the sensor element 101 has a configuration in which the inner pump electrode 22 is not located between the heater part 70 and the first internal space 20 in the thickness direction of the element.

As the inner pump electrode 22 is heated to a higher temperature, Au is more likely to evaporate from the inner pump electrode 22, and thus NOx essentially to be decomposed by the measurement electrode 44 is more likely to be decomposed by the inner pump electrode 22. Decomposition of NOx before the measurement gas reaches the measurement electrode 44 is not preferable because the magnitude of the NOx current flowing through the measurement pump cell 41 does not correctly reflect the NOx concentration of the measurement gas. In addition, evaporating Au is attached to the measurement electrode 44 or to the fourth diffusion control part 45 formed thereon to prevent the measurement gas from reaching the measurement electrode 44. As a result, NOx measurement accuracy (also referred to as NOx sensitivity) tends to be reduced with continuous use of the gas sensor 100. Evaporation of Au from the inner pump electrode 22 is a phenomenon occurring at random, so that NOx sensitivity reduction behavior varies from individual to individual. A degree of evaporation of Au also varies with usage history of an individual gas sensor. This means that the variation in NOx sensitivity among gas sensors manufactured on the same condition increases with continuous use of each of the gas sensors.

In the sensor element 101 according to the present embodiment, evaporation of Au from the inner pump electrode 22 is suppressed by disposing the inner pump electrode 22 only on the lower surface of the second solid electrolyte layer 6 opposing the region 22β in the first internal space 20 and maintained at a slightly lower temperature than the region 22β when the sensor element 101 is in use, as described above. In the gas sensor 100, the influence of evaporation of Au is reduced, thereby to suppress reduction in NOx sensitivity due to continuous use. Furthermore, the increase in variation in NOx sensitivity is suppressed.

However, the area of the inner pump electrode 22 in a configuration in which the inner pump electrode 22 is located only on the lower surface of the second solid electrolyte layer 6 as in the present embodiment is naturally smaller than the total area of the inner pump electrode 22 in a case where the inner pump electrode 22 is provided not only on the lower surface but also in the region 22B. The main pump voltage Vp0 applied to the main pump cell 21 in a case where oxygen is pumped out from the measurement gas having flowed into the first internal space 20 to achieve predetermined oxygen partial pressure in the first internal space 20 is higher in a case where the inner pump electrode 22 is not provided in the region 22β than in a case where the inner pump electrode 22 is provided in the region 22β as long as an aspect of the flow of the measurement gas into the first internal space 20 (e.g., an oxygen concentration, a flow rate, and a flow velocity) and target oxygen partial pressure are the same. This is because the amount of pumped-out oxygen per unit area is required to be increased as the electrode has a smaller area.

An excessive increase in main pump voltage Vp0 applied to the main pump cell 21, however, is not preferable because decomposition of NOx occurs in the main pump cell 21 and the NOx concentration measurement accuracy of the gas sensor 100 is resultantly reduced, in particular, in a case where the measurement gas has a high oxygen concentration, as in a case where Au evaporates from the inner pump electrode 22.

In the present embodiment, a degree of such decomposition of NOx in the main pump cell 21 is to be evaluated based on a degree of linearity between the NOx current Ip2 and the oxygen concentration. More particularly, it is already found that, in a case that evaporation of Au has not yet occurred in a gas sensor, there is a linear change of a monotonous increase between the NOx current Ip2 and the oxygen concentration of the measurement gas, and, once decomposition of NOx occurs in the main pump cell 21, deviation from the linearity becomes pronounced in a high oxygen concentration range. The degree of linearity between the NOx current Ip2 and the oxygen concentration can be evaluated by the magnitude of a determination coefficient (a value of the square of a correlation coefficient) $R^2$. It is determined that there is good linearity between the NOx current Ip2 and the oxygen concentration as a value of the determination coefficient is closer to one.

In view of the foregoing, in the present embodiment, a model gas containing 18% of oxygen and the balance being nitrogen is prepared as an evaluation gas, and the magnitude of a current density of a current flowing through the main pump cell 21 (a main pump cell current density) when the gas sensor 100 is operated with the evaluation gas introduced into the gas distribution part is used as an indicator of a pumping ability of the main pump cell 21 in the sensor element 101. The element driving temperature at evaluation is set to 850° C., and the electromotive force V1 in the auxiliary sensor cell 81 is set to 385 mV so that the oxygen partial pressure in the second internal space 40 is constant.

It is determined that pumping can desirably be performed while decomposition of NOx is desirably suppressed, if the main pump cell current density is 0.4 mA/mm$^2$ or less.

A requirement that the main pump cell current density is 0.4 mA/mm$^2$ or less can specifically be fulfilled, for example, in a manner that the area of the inner pump electrode 22 on the lower surface of the second solid electrolyte layer 6 is increased within a possible range, or, in a manner that the first diffusion control part 11 and the second diffusion control part 13 are configured so that the flow velocity of the measurement gas from the gas inlet 10 to the first internal space 20 is reduced without causing any problems in securing responsiveness.

<Shape of Second Diffusion Control Part and Flow of Measurement Gas>

The form of the second diffusion control part 13 that can additionally be used for the sensor element 101 will be described next.

As described above, the sensor element 101 according to the present embodiment has a configuration in which the inner pump electrode 22 is disposed only on the lower surface of the second solid electrolyte layer 6, and preferably has a configuration in which the main pump cell current density is 0.4 mA/mm$^2$ or less.

In particular, in a case where the latter configuration is used, an excessive increase in main pump voltage Vp0 applied between the inner pump electrode 22 and the outer pump electrode 23 is suppressed. This functional effect, however, can strictly be recognized in a case where the inner pump electrode 22 is considered to be equalized as a whole in pumping out of oxygen from the inner pump electrode 22 (i.e., in a case where it is considered that oxygen is uniformly pumped out from the inner pump electrode 22).

In the actual sensor element 101, pumping out of oxygen from the inner pump electrode 22 is more likely to occur at a location closer to the second diffusion control part 13 as an opening through which the measurement gas flows into the first internal space 20. Thus, even in a case where the main pump cell current density is 0.4 mA/mm$^2$ or less, a locally high voltage might be applied between a portion of the inner pump electrode 22 closer to the second diffusion control part 13 and the outer pump electrode 23, thereby to cause decomposition of NOx.

Figure 2A:
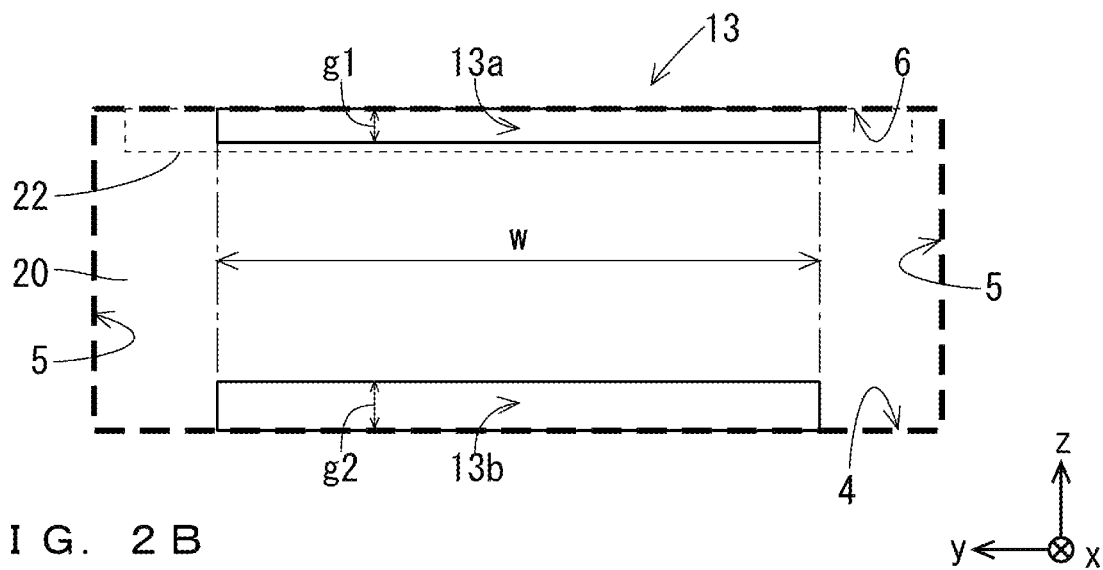
FIGS. 2A and 2B illustrate one aspect of a configuration of a second diffusion control part 13 intended to improve non-uniformity of a voltage applied to an inner pump electrode 22.
Figure 2B:
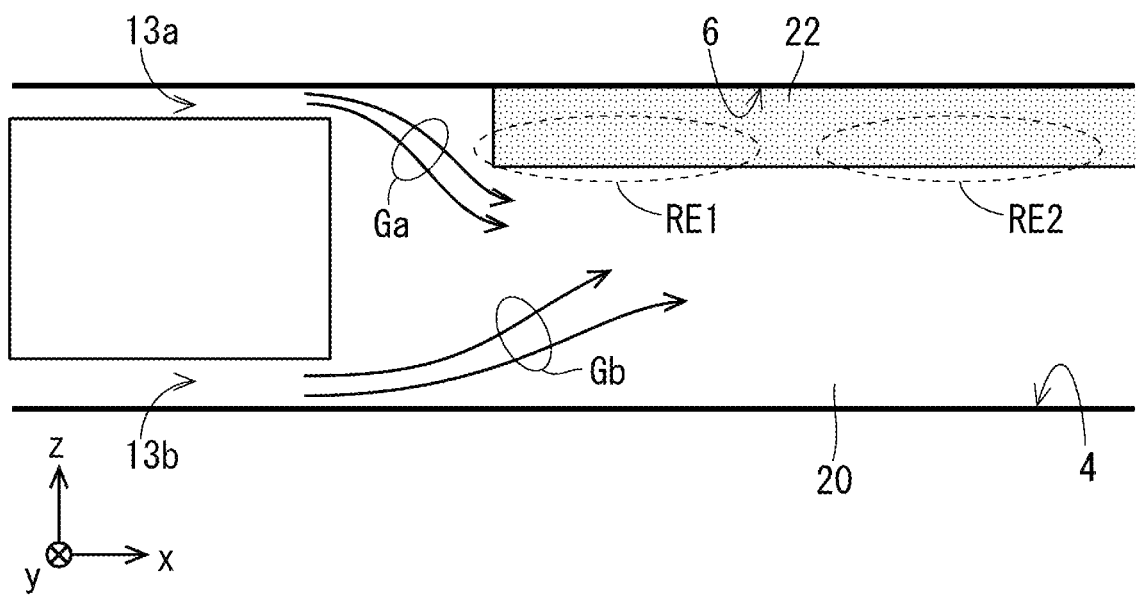

FIGS. 2A and 2B illustrate one aspect of a configuration of the second diffusion control part 13 intended to improve such non-uniformity of the voltage applied to the inner pump electrode 22. FIG. 2A is a sectional view (yz sectional view) of the second diffusion control part 13 perpendicular to the longitudinal direction of the element (x-axis direction), and FIG. 2B is a vertical sectional view (zx sectional view) along the longitudinal direction of the element (x-axis direction) from the second diffusion control part 13 to the inner pump electrode 22 in the first internal space 20. The locations of the first internal space 20 and the inner pump electrode 22 are overlaid in FIG. 2A (the same applies to FIGS. 3 and 4A).

In a case illustrated in FIG. 2A, the upper slit 13a and the lower slit 13b constituting the second diffusion control part 13 have the same width w, but, in the thickness direction of the element (z-axis direction), the lower slit 13b farther from the inner pump electrode 22 has a gap g2 larger than a gap g1 of the upper slit 13a closer to the inner pump electrode 22. The lower slit 13b is thereby larger than the upper slit 13a in the second diffusion control part 13. In this case, a ratio of diffusion resistance D1 at the upper slit 13a to diffusion resistance D2 at the lower slit 13b is the inverse of a ratio of the gap g1 of the former to the gap g2 of the latter. That is to say, D1/D2=g2/g1. In a case where the second diffusion control part 13 has such a configuration, the measurement gas flowing into the first internal space 20 through the second diffusion control part 13 has a gas stream Gb passing through the lower slit 13b with a higher flow velocity than a gas stream Ga passing through the upper slit 13a, as illustrated in FIG. 2B. The gas stream Ga thus becomes closer to a region RE1 (on the negative side in the x-axis direction) of the inner pump electrode 22 closer to the upper slit 13a, but the gas stream Gb is more likely to flow toward a region RE2 (on the positive side in the x-axis direction) of the inner pump electrode 22 at the back in the first internal space 20 due to a combination of the magnitude of the flow velocity thereof and the arrangement of the lower slit 13b and the inner pump electrode 22. In other words, it can be said that the configuration illustrated in FIGS. 2A and 2B is a configuration to guide the measurement gas flowing into the internal space 20 through the lower slit 13b to the back.

In a case where the configuration in FIGS. 2A and 2B is used, local application of the main pump voltage Vp0 in the region RE1 closer to the second diffusion control part 13 is avoided to level pumping out of oxygen in the inner pump electrode 22, so that application of a locally high main pump voltage Vp0 between the region RE1 and the outer pump electrode 23 to cause decomposition of NOx is desirably suppressed. The gas sensor 100 in which a change in NOx sensitivity over time is small is thereby achieved.

Figure 3:
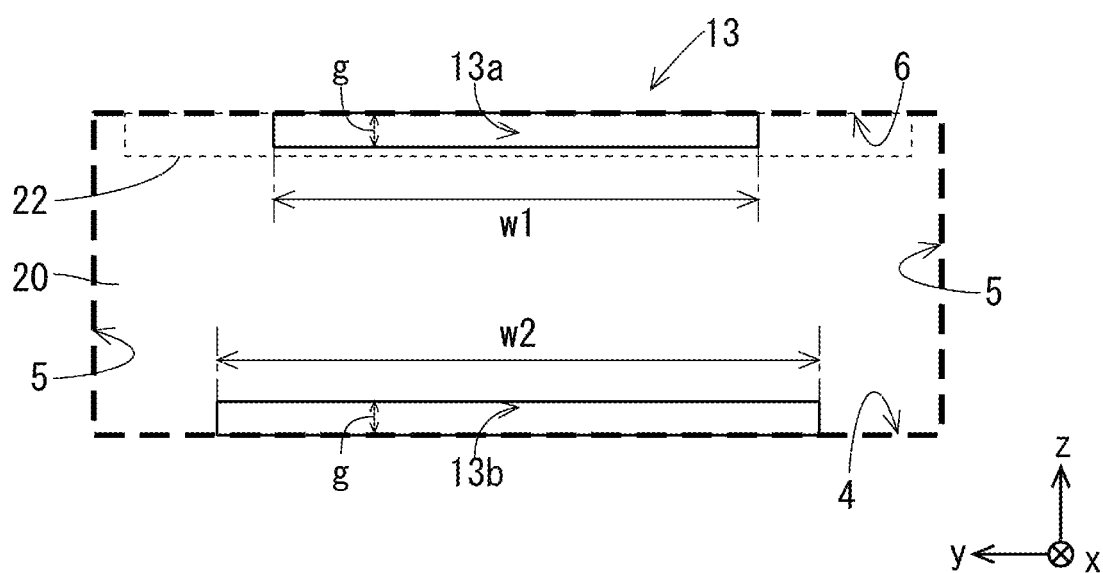
FIG. 3 illustrates another aspect of the configuration of the second diffusion control part 13 intended to improve non-uniformity of the voltage applied to the inner pump electrode 22.

FIG. 3 is a sectional view (yz sectional view) of the second diffusion control part 13 perpendicular to the longitudinal direction of the element (x-axis direction) illustrating another aspect of the configuration of the second diffusion control part 13 intended to improve non-uniformity of the voltage applied to the inner pump electrode 22.

In a case illustrated in FIG. 3, the upper slit 13a and the lower slit 13b constituting the second diffusion control part 13 have the same gap g in the thickness direction of the element (z-axis direction), but, in the width direction of the element (y-axis direction), the lower slit 13b farther from the inner pump electrode 22 has a width w2 greater than a width w1 of the upper slit 13a closer to the inner pump electrode 22. The lower slit 13b is thereby larger than the upper slit 13a in the second diffusion control part 13. In this case, the ratio of the diffusion resistance D1 at the upper slit 13a to the diffusion resistance D2 at the lower slit 13b is the inverse of a ratio of the width w1 of the former to the width w2 of the latter. That is to say, D1/D2=w2/w1.

Also in a case where the second diffusion control part 13 has such a configuration, the measurement gas flowing into the first internal space 20 through the second diffusion control part 13 has the gas stream Gb passing through the lower slit 13b with a higher flow velocity than the gas stream Ga passing through the upper slit 13a, as in a case of FIGS. 2A and 2B. That is to say, it can be said that the configuration illustrated in FIG. 3 is also the configuration to guide the measurement gas flowing into the internal space 20 through the lower slit 13b to the back.

Also in a case where the configuration in FIG. 3 is used, local application of the main pump voltage Vp0 in the region RE1 closer to the second diffusion control part 13 is avoided to level pumping out of oxygen in the inner pump electrode 22, so that application of the locally high main pump voltage Vp0 between the region RE1 and the outer pump electrode 23 to cause decomposition of NOx is desirably suppressed. Also in this case, the gas sensor 100 in which the change in NOx sensitivity over time is small is achieved.

As yet another aspect, the upper slit 13a and the lower slit 13b may have different gaps and different widths to level pumping out of oxygen in the inner pump electrode 22.

In the sensor element 101 in which the second diffusion control part 13 is composed of the upper slit 13a and the lower slit 13b in cases as illustrated in FIGS. 1 to 3 including the above-mentioned case, the diffusion resistance ratio D1/D2 between them preferably satisfies D1/D2>1 to avoid local application of the main pump voltage Vp0 between the portion of the inner pump electrode 22 closer to the second diffusion control part 13 and the outer pump electrode 23. The effect becomes more pronounced at least when D1/D2>1.5.

An upper limit of the diffusion resistance ratio D1/D2 is determined by a trade-off between minimum allowed values of the gap and the width of the upper slit 13a and maximum allowed values of the gap and the width of the lower slit 13b, but at least the sensor element 101 in which the diffusion resistance ratio D1/D2 is approximately 1.1 to 5 can be manufactured without any problems. It is of course preferable to meet the requirement that the main pump cell current density is 0.4 mA/mm$^2$ or less in this case.

Figure 4A:
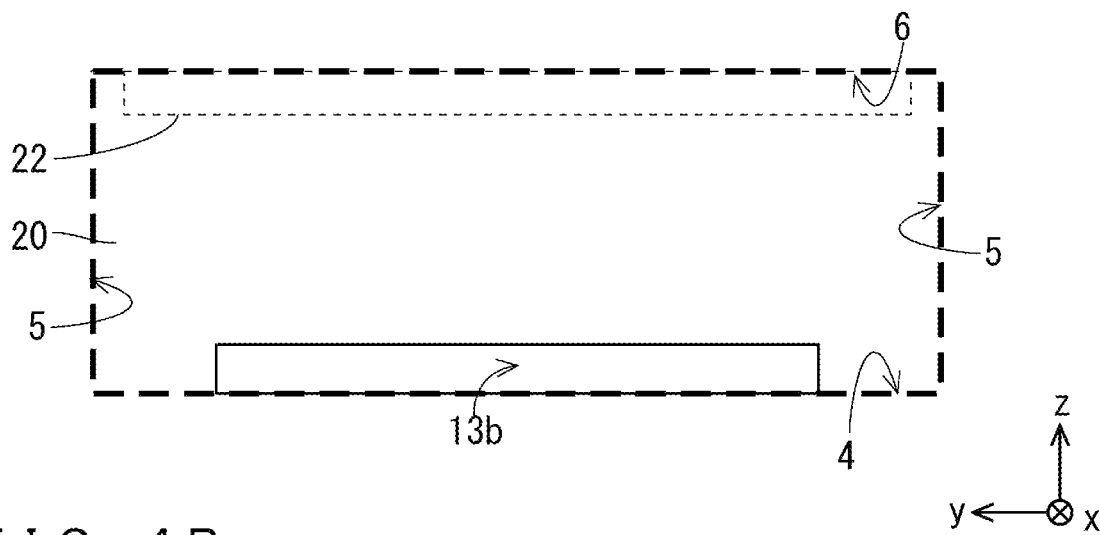
FIGS. 4A and 4B illustrate a configuration in which the second diffusion control part 13 includes only a lower slit 13$b$.
Figure 4B:
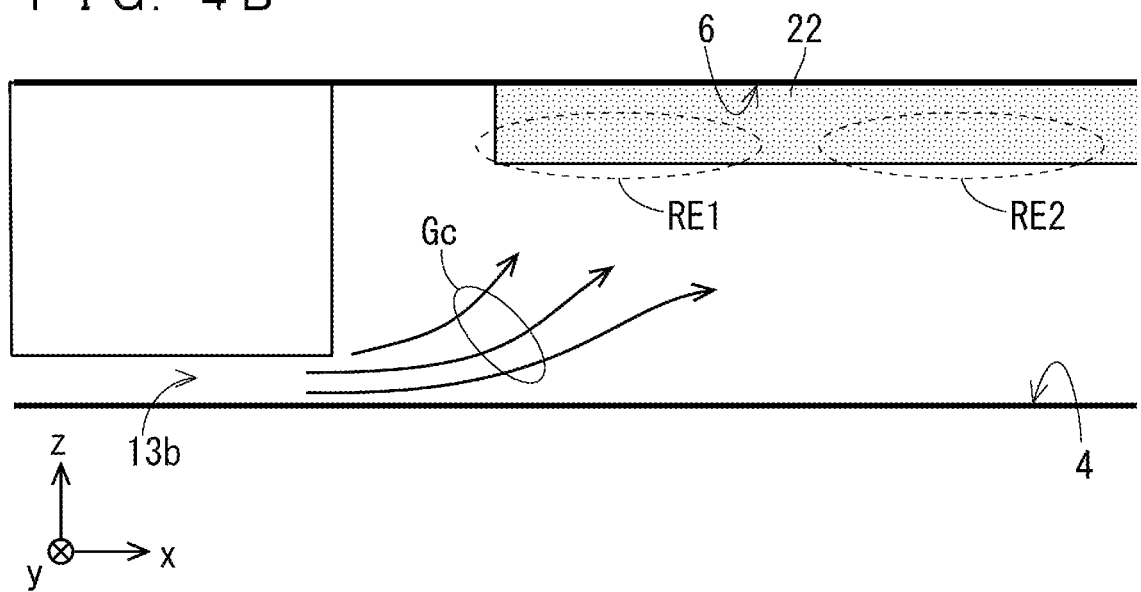

Alternatively, as another aspect, a configuration in which the upper slit 13a is not provided so that the second diffusion control part 13 includes only the lower slit 13b may be used. FIGS. 4A and 4B illustrate such a configuration in which the second diffusion control part 13 includes only the lower slit 13b. FIG. 4A is a sectional view of the second diffusion control part 13 perpendicular to the longitudinal direction of the element, and FIG. 4B is a vertical sectional view along the longitudinal direction of the element from the second diffusion control part 13 to the inner pump electrode 22 in the first internal space 20.

In a case where the second diffusion control part 13 has such a configuration, the measurement gas naturally flows into the first internal space 20 only through the lower slit 13b as illustrated in FIG. 4B. The lower slit 13b is separated from the inner pump electrode 22 in the thickness direction of the element, so that a gas stream Gc in this case flows not only toward the region RE1 (on the negative side in the x-axis direction) of the inner pump electrode 22 closer to the upper slit 13a but also toward the region RE2 (on the positive side in the x-axis direction) of the inner pump electrode 22 at the back of the region RE1. That is to say, the configuration illustrated in FIGS. 4A and 4B is also the configuration to guide the measurement gas flowing into the internal space 20 through the lower slit 13b to the back.

Also in a case where the configuration in FIGS. 4A and 4B is used, local application of the main pump voltage Vp0 in the region RE1 closer to the second diffusion control part 13 is avoided to level pumping out of oxygen in the inner pump electrode 22, so that application of the locally high main pump voltage Vp0 between the region RE1 and the outer pump electrode 23 to cause decomposition of NOx is desirably suppressed. The gas sensor 100 in which the change in NOx sensitivity over time is small is achieved. It is of course preferable to meet the requirement that the main pump cell current density is 0.4 mA/mm$^2$ or less also in this case.

<Extension of Inner Pump Electrode>

In the sensor element 101 illustrated in FIG. 1, the inner pump electrode 22 is provided only on the lower surface of the second solid electrolyte layer 6 to suppress evaporation of Au occurring with a temperature rise by the heater part 70. In a case where the configuration is used, however, the inner pump electrode 22 has a smaller area compared with a case where the inner pump electrode 22 is provided also in the region 22B, and thus an excessive increase in main pump voltage Vp0 might be caused.

Figure 5:
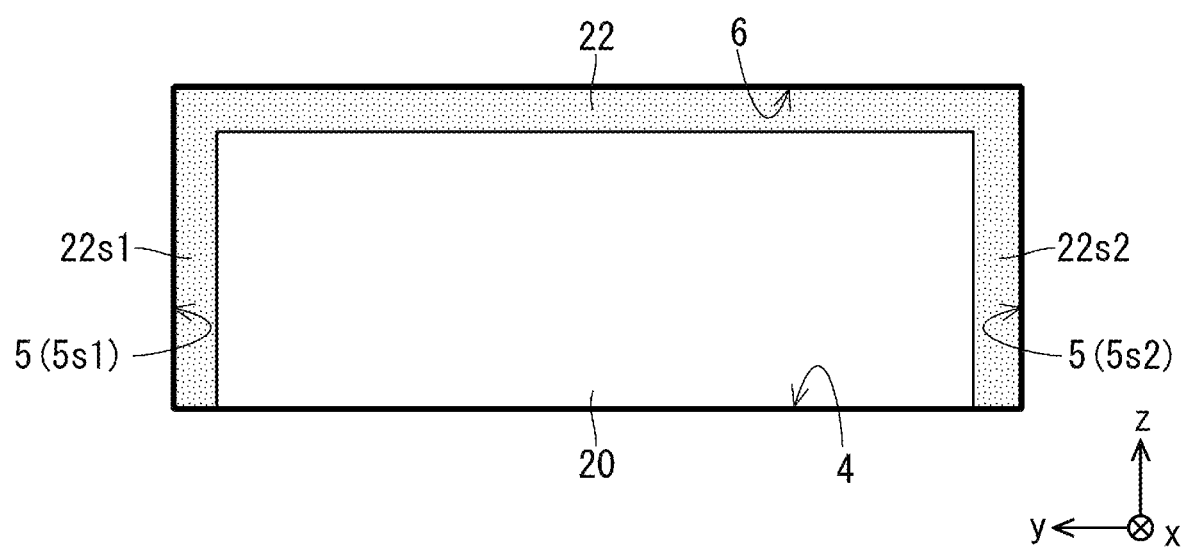
FIG. 5 illustrates another aspect of the inner pump electrode 22.

One of measures against the excessive increase in voltage is to also use the configuration in which the main pump cell current density is 0.4 mA/mm$^2$ or less as described above, but the excessive increase in voltage can be addressed also by using a configuration illustrated in FIG. 5. FIG. 5 is a sectional view (yz sectional view) of the inner pump electrode 22 perpendicular to the longitudinal direction of the element (x-axis direction) illustrating another aspect of the inner pump electrode 22.

Specifically, the inner pump electrode 22 illustrated in FIG. 5 includes two extensions 22s1 and 22s2 extending from the lower surface of the second solid electrolyte layer 6 to respective two surfaces 5s1 and 5s2 of the spacer layer 5 that are surfaces defining the first internal space 20 and being along the longitudinal direction and the thickness direction of the element (surfaces parallel to a zx plane).

Due to the presence of the extensions 22s1 and 22s2, the inner pump electrode 22 has a larger area compared with a case where the inner pump electrode 22 is formed only on the lower surface of the second solid electrolyte layer 6, so that an excessive increase in main pump voltage Vp0 is desirably suppressed.

It is not necessary to include both the extensions 22s1 and 22s2, and only one of the extensions 22s1 and 22s2 may be formed.

A configuration in which the inner pump electrode 22 includes the extensions 22s1 and 22s2, and the main pump cell current density is 0.4 mA/mm$^2$ or less may be used.

<Process of Manufacturing Sensor Element>

A process of manufacturing the sensor element 101 having a configuration and features as described above will be described next. In the present embodiment, a laminated body of green sheets containing an oxygen-ion conductive solid electrolyte, such as zirconia, as a ceramic component is formed, and cut and fired to manufacture the sensor element 101.

A case where the sensor element 101 including the six layers illustrated in FIG. 1 is manufactured will be described as an example below. In this case, six green sheets corresponding to the first substrate layer 1, the second substrate layer 2, the third substrate layer 3, the first solid electrolyte layer 4, the spacer layer 5, and the second solid electrolyte layer 6 are to be prepared. FIG. 6 is a flowchart showing processing when the sensor element 101 is manufactured.

In a case where the sensor element 101 is manufactured, blank sheets (not illustrated) being green sheets having no pattern formed thereon are prepared first (step S1). In a case where the sensor element 101 including the six layers is manufactured, six blank sheets are prepared to correspond to the respective layers.

The blank sheets have a plurality of sheet holes used for positioning in printing and lamination. The sheet holes are formed to the blank sheets in advance prior to pattern formation through, for example, punching by a punching machine. Green sheets corresponding to layers constituting an internal space also include penetrating portions corresponding to the internal space formed in advance through, for example, punching as described above. The blank sheets corresponding to the respective layers of the sensor element 101 are not required to have the same thickness.

When the blank sheets corresponding to the respective layers are prepared, pattern printing and drying are performed on the individual blank sheets (step S2). Specifically, a pattern of various electrodes, a pattern of the fourth diffusion control part 45, a pattern of the heater element 72 and the heater insulating layer 74, a pattern of internal wiring, which is not illustrated, and the like are formed. In particular, in forming each of the patterns, the patterns are applied at predetermined locations so that the various electrodes, each component of the heater part 70, the internal wiring, and the like eventually formed satisfy desired sizes.

Application or disposition of a sublimable material for forming the first diffusion control part 11, the second diffusion control part 13, and the third diffusion control part 30 is also performed at the time of pattern printing. In a case where the two slits (the upper slit 13a and the lower slit 13b) of the second diffusion control part 13 have different sizes (at least one of widths and gaps), application or disposition of the sublimable material is performed to allow for the sizes.

The patterns are printed by applying pastes for pattern formation prepared in accordance with characteristics required for respective formation targets onto the blank sheets using known screen printing technology. A known drying means can be used for drying after printing.

When pattern printing on each of the blank sheets ends, printing and drying of a bonding paste are performed to laminate and bond the green sheets corresponding to the respective layers (step S3). The known screen printing technology can be used for printing of the bonding paste, and the known drying means can be used for drying after printing.

The green sheets to which the bonding agent has been applied are then stacked in a predetermined order, and the stacked green sheets are crimped under a predetermined temperature and pressure condition to thereby form a laminated body (step S4). Specifically, crimping is performed by stacking and holding the green sheets as a target of lamination on a predetermined lamination jig, which is not illustrated, while positioning the green sheets at the sheet holes, and then heating and pressurizing the green sheets together with the lamination jig using a lamination machine, such as a known hydraulic pressing machine. The pressure, temperature, and time for heating and pressurizing depend on a lamination machine to be used, and an appropriate condition is determined to achieve good lamination.

When the laminated body is obtained as described above, the laminated body is then cut at a plurality of locations into units (referred to as element bodies) to become individual sensor elements 101 (step S5).

The cut element bodies are each fired at a firing temperature of approximately 1300° C. to 1500° ° C. (step S6). The sensor element 101 is thereby manufactured. That is to say, the sensor element 101 is generated through integral firing of the solid electrolyte layers and the electrodes. The firing temperature in this case is preferably 1200° C. or more and 1500° C. or less (e.g., 1400°) C. Integral firing is performed in this manner, so that the electrodes each have sufficient adhesion strength in the sensor element 101.

In a case where the inner pump electrode 22 includes the extensions 22s1 and 22s2 as illustrated in FIG. 5, after a through hole corresponding to the first internal space 20 is formed to a green sheet corresponding to the spacer layer 5 in advance through, for example, punching by a punching machine, an electrode paste for forming the extensions 22s1 and 22s2 is poured into the through hole by screen printing and the like before lamination of the green sheet.

The sensor element 101 thus obtained is housed in a predetermined housing, and built into the body (not illustrated) of the gas sensor 100.

As described above, according to the present embodiment, the inner pump electrode as the cermet electrode of the Pt—Au alloy and $ZrO_2$ forming the main pump cell to pump out oxygen from the internal space in the sensor element of the gas sensor is provided, from among the two surfaces opposing each other in the thickness direction of the element in the internal space, only on the surface farther from the heater part, and is not provided at a location where Au is likely to evaporate due to heating of the sensor element by the heater part when the gas sensor is in use, so that the gas sensor in which deterioration of the NOx sensitivity over time is suppressed even in a case where the gas sensor is in continuous use is achieved.

The sensor element preferably has the configuration in which the main pump cell current density is 0.4 mA/mm$^2$ or less, so that an excessive increase in main pump voltage applied to the main pump cell to cause decomposition of NOx in a case where the oxygen concentration is high is suppressed.

Furthermore, in a case where the configuration to guide the measurement gas flowing into the internal space through the lower slit to the back is used as the configuration of a slit-like diffusion control part allowing the measurement gas to flow into the internal space, pumping out of oxygen in the inner pump electrode is leveled, and application of the locally high main pump voltage between the region of the inner pump electrode closer to the diffusion control part and the outer pump electrode to cause decomposition of NOx is desirably suppressed.

Modification

In the above-mentioned embodiment, the measurement electrode 44 is disposed in the second internal space 40 to be covered with the fourth diffusion control part 45 functioning as the porous protective film and providing the predetermined diffusion resistance to the measurement gas, and the amount of NOx flowing into the measurement electrode 44 is limited by the fourth diffusion control part 45. Alternatively, however, a third internal space communicating with the second internal space 40, for example, through a slit-like or porous diffusion control part providing, to the measurement gas, diffusion resistance equivalent to the diffusion resistance provided by the fourth diffusion control part 45 may be provided, and the measurement electrode 44 may be provided in the third internal space.

Figure 7:
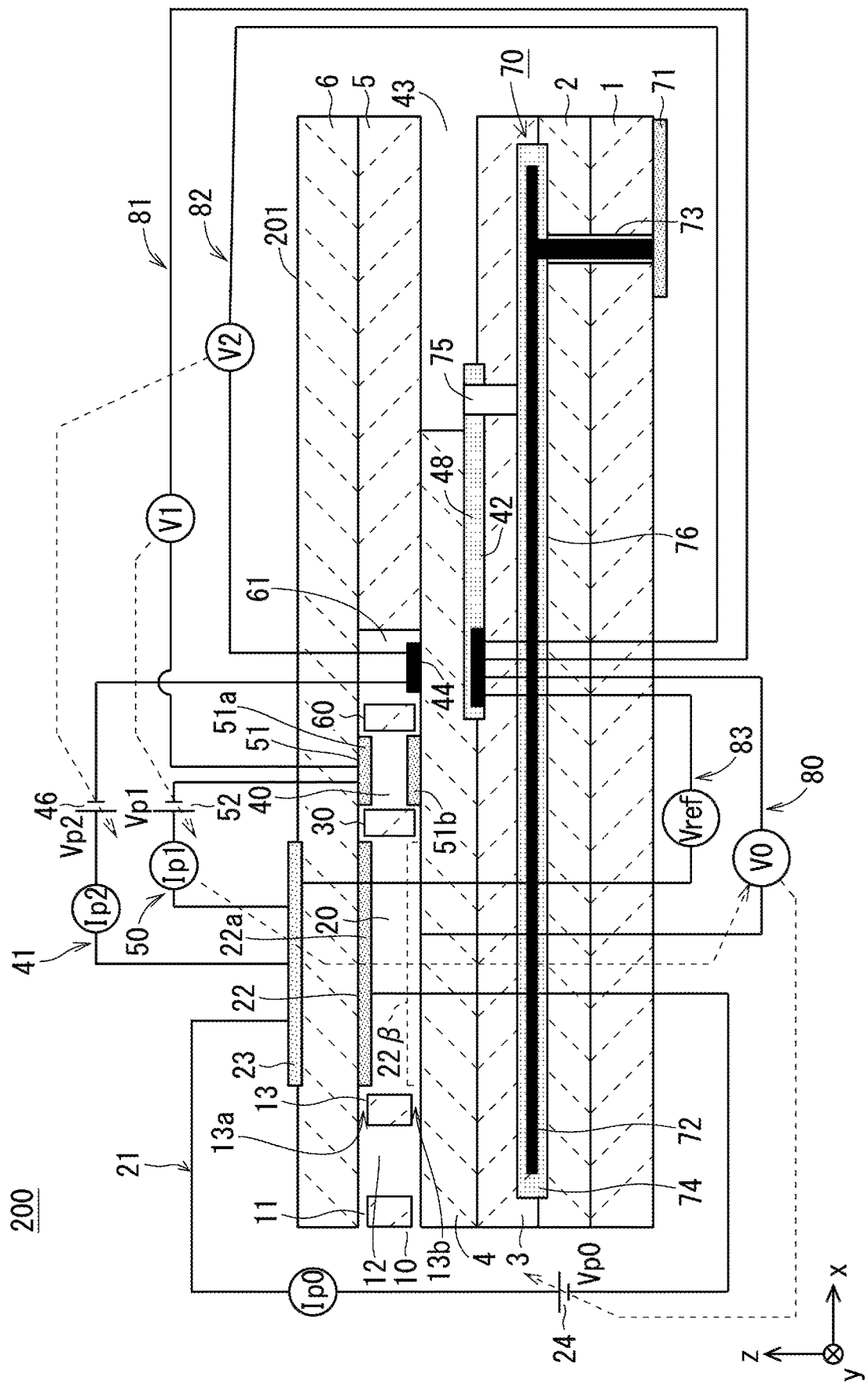
FIG. 7 schematically shows one example of a configuration of a gas sensor 200 including a vertical sectional view taken along a longitudinal direction of a sensor element 201.

FIG. 7 schematically shows one example of a configuration of a gas sensor 200 including a vertical sectional view taken along a longitudinal direction of a sensor element 201 having such a configuration. The sensor element 201 includes components having action and functions in common with the components of the sensor element 101 illustrated in FIG. 1. Such components bear the same reference signs as those of the corresponding components illustrated in FIG. 1, and detailed description thereof is omitted unless it is necessary. The controller 110 is not illustrated.

The sensor element 201 is different from the sensor element 101 illustrated in FIG. 1 in that the first diffusion control part 11 doubles as the gas inlet 10, a third internal space 61 communicating with the second internal space 40 through a slit-like fifth diffusion control part 60 similar to the first diffusion control part 11, the second diffusion control part 13, and the third diffusion control part 30 is provided, the measurement electrode 44 is provided on an upper surface of a portion of the first solid electrolyte layer 4 facing the third internal space 61, and the measurement electrode 44 is exposed to the third internal space 61. The sensor element 201, however, is similar to the sensor element 101 in that a diffusion control part is located between the second internal space 40 and the measurement electrode 44.

In the sensor element, the inner pump electrode is provided in a similar manner to that in the above-mentioned embodiment, so that the influence of evaporation of Au from the inner pump electrode on the NOx sensitivity due to continuous use is reduced. Furthermore, the effect obtained in a case where the sensor element has the configuration in which the main pump cell current density is 0.4 mA/mm² or less and, further, the effect obtained by using the configuration to guide the measurement gas flowing into the internal space 20 through the lower slit to the back of the internal space as illustrated in FIGS. 2A, 2B, 3, 4A, and 4B and the configuration in which the inner pump electrode 22 has the extensions as illustrated in FIG. 5 can similarly be obtained.

Examples (Evaluation 1: Evaluation of NOx Sensitivity Change Rate Before and After Durability Test in Air)

Five gas sensors 100 (Examples 1 to 5) according to the above-mentioned embodiment were manufactured on the same manufacturing condition, and, on each of the gas sensors 100, a durability test in air to continuously drive the gas sensor 100 under an air atmosphere for 3000 hours was conducted, and the NOx current Ip2 was measured under a model gas atmosphere having a NOx concentration of 500 ppm and the balance being nitrogen using a model gas apparatus before and after driving. The element driving temperature was set to 850° C.

In the sensor element 101 of each of the gas sensors 100, the inner pump electrode 22 was provided only on the lower surface of the second solid electrolyte layer 6 to have an area of 7.5 mm². The second diffusion control part 13 included the upper slit 13a and the lower slit 13b each having a width of 2000 μm and a gap of 10 μm. The main pump cell current density in the obtained sensor element 101 was 0.4 mA/mm².

Before and after the start of the durability test in air, the slope of the sensitivity characteristics (a change rate of the NOx current to a value of the NO concentration) was respectively calculated by dividing a measured value of the NOx current Ip2 by the NO concentration (500 ppm), and further, a change rate of the slope after the test with respect to the slope before the test as a reference (an initial value) was calculated as the NOx sensitivity change rate.

Five gas sensors (Conventional Examples 1 to 5) having a similar configuration to that of Examples 1 to 5 except that the inner pump electrode 22 was provided not only on the lower surface of the second solid electrolyte layer 6 but also in the region 22β (a conventional configuration) were manufactured on the same manufacturing condition. On each of the gas sensors, the durability test in air, measurement of the NOx current Ip2, and calculation of the NOx sensitivity change rate were conducted in a similar manner to Examples 1 to 5.

The NOx sensitivity change rates of the gas sensors 100 of Examples 1 to 5 and Conventional Examples 1 to 5, an average value and the standard deviation of the NOx sensitivity change rates of Examples 1 to 5, and an average value and the standard deviation of the NOx sensitivity change rates of Conventional Examples 1 to 5 are shown in Table 1 as a list.

TABLE 1

| LEVEL | NOx SENSITIVITY CHANGE RATE [%] | AVERAGE | STANDARD DEVIATION |
|---|---|---|---|
| EXAMPLE 1 | −8.1 | −8.0 | 0.6 |
| EXAMPLE 2 | −7.2 | | |
| EXAMPLE 3 | −8.8 | | |
| EXAMPLE 4 | −7.6 | | |
| EXAMPLE 5 | −8.4 | | |

TABLE 1-continued

| LEVEL | NOx SENSITIVITY CHANGE RATE [%] | AVERAGE | STANDARD DEVIATION |
|---|---|---|---|
| CONVENTIONAL EXAMPLE 1 | −13.9 | −16.8 | 3.1 |
| CONVENTIONAL EXAMPLE 2 | −17.3 | | |
| CONVENTIONAL EXAMPLE 3 | −22.5 | | |
| CONVENTIONAL EXAMPLE 4 | −15.3 | | |
| CONVENTIONAL EXAMPLE 5 | −14.9 | | |

As can be seen from Table 1, the absolute values of the NOx sensitivity change rates and the standard deviation of Examples 1 to 5 are smaller than those of Conventional Examples 1 to 5. The results indicate that, in a case where the sensor element 101 has the configuration in which the inner pump electrode 22 is provided only on the lower surface of the second solid electrolyte layer 6 as in the above-mentioned embodiment, deterioration of the NOx sensitivity due to long-term or continuous use is suppressed compared with a case where the inner pump electrode 22 is provided also in the region 22. This is considered to suggest that, when the inner pump electrode 22 is not provided in the region 22β heated to a high temperature by the heater part 70, evaporation of Au from the inner pump electrode 22 due to heating is desirably suppressed.

(Evaluation 2: Evaluation of NOx Sensitivity Change Rate Before and After Diesel Engine Test)

Six types of gas sensors 100 having different configurations of the sensor element 101 including the gas sensor 100 of Example 1 in Evaluation 1 (Example 1 and Examples 6 to 10) were manufactured, and a diesel engine durability test was conducted on each of the gas sensors 100 to evaluate the NOx sensitivity change rate and dependency of the NOx current on the oxygen concentration after the diesel engine durability test.

In each of the gas sensors 100 of Examples 1, 6, and 7, the gas distribution part had a configuration in which the inner pump electrode 22 of the sensor element 101 was provided only on the lower surface of the second solid electrolyte layer 6, and had an area of 7.5 mm², while main pump currents Ip0 of 3.0 mA, 2.5 mA, and 4.0 mA were allowed to flow, respectively. Main pump cell current densities were thus 0.4 mA/mm², 0.33 mA/mm², and 0.53 mA/mm² in the gas sensors 100 of Examples 1, 6, and 7, respectively.

The gas sensor 100 of Example 8 was the same as the gas sensor 100 of Example 1 except that the inner pump electrode 22 had an area of 10.0 mm².

On the other hand, the gas sensors of Examples 9 and 10 were each the same as the gas sensor 100 of Example 1 except that the gas distribution part had a configuration in which the inner pump electrode 22 of the sensor element 101 included the extensions 22s1 and 22s2, the inner pump electrodes 22 had areas of 10.0 mm² and 15.0 mm², respectively, and the main pump current Ip0 of 4.0 mA was allowed to flow.

A gas sensor (Conventional Example 6) having a similar configuration to that of the Example 1 except that the inner pump electrode 22 was provided not only on the lower surface of the second solid electrolyte layer 6 but also in the region 22β on the upper surface of the first solid electrolyte layer 4 (the conventional configuration) was manufactured. The diesel engine durability test was conducted on each of the gas sensors in a similar manner to Example 1 and Examples 6 to 10 to evaluate the NOx sensitivity change rate and the dependency of the NOx current on the oxygen concentration after the diesel engine durability test.

The diesel engine durability test was conducted on a condition below: Each of the gas sensors 100 was installed onto an exhaust pipe of an engine, and a 40-minute driving pattern configured to have an engine speed in a range of 1500 rpm to 3500 rpm and a load torque in a range of 0 N·m to 350 N·m was repeated until 3000 hours had elapsed. In this case, the temperature of the gas was maintained within a range of 200° ° C. to 600° C., and the NOx concentration was set to have a value within a range of 0 ppm to 1500 ppm.

The NOx current Ip2 was measured using model gases before the start, at 1000 hours after the start, at 2000 hours after the start, and at the end (at 3000 hours after the start) of the diesel engine durability test.

The model gas measurement was performed using four model gases having different oxygen concentrations of 0%, 5%, 10%, and 18% while having a constant NO concentration of 500 ppm (the balance being $N_2$ in each of the model gases). The element driving temperature was set to 850° C. in each case.

The NOx sensitivity change rate was calculated as in Evaluation 1 using the NO concentration (500 ppm) in a case where the oxygen concentration was 0% and the measured value of the NOx current Ip2 at the NO concentration at each of the above-mentioned time points.

Figure 8:
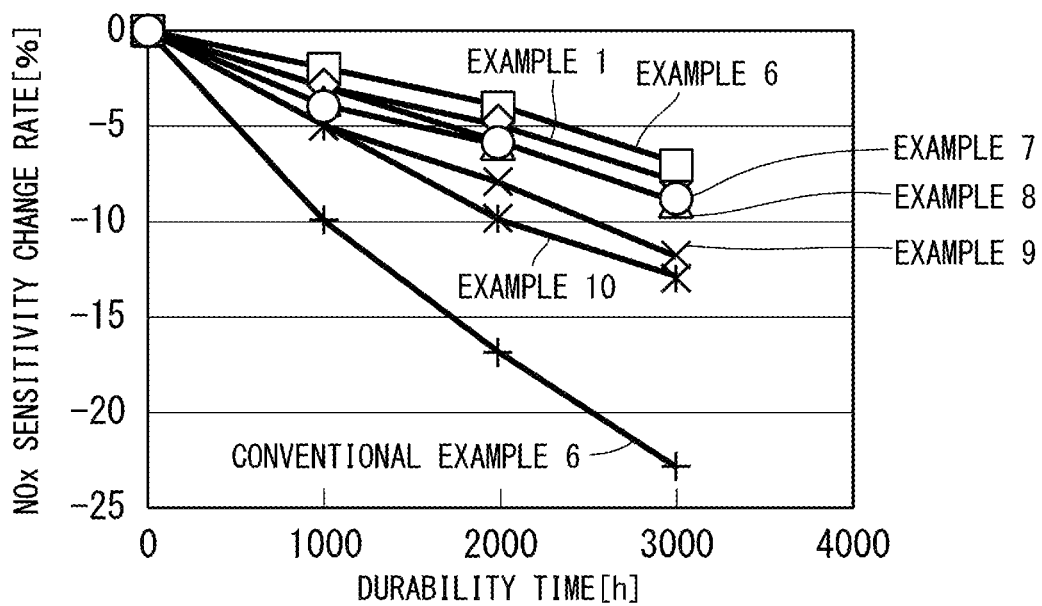
FIG. 8 is a plot of NOx sensitivity change rates of gas sensors of Example 1, Examples 6 to 10, and Conventional Example 6 against durability times.

FIG. 8 is a plot of NOx sensitivity change rates of the gas sensors of Example 1, Examples 6 to 10, and Conventional Example 6 against elapsed times (durability times) of the diesel engine durability test.

It can be seen from FIG. 8 that, while (the absolute value of) the NOx sensitivity change rate of each of the gas sensors monotonously changes with elapsed time of the diesel engine durability test, the absolute value of the NOx sensitivity change rate of each of the gas sensors 100 of Example 1 and Examples 6 to 10 is limited to 15% or less even after the elapse of 3000 hours, whereas the absolute value of the NOx sensitivity change rate of the gas sensor 100 of Conventional Example 6 exceeds 20%.

The determination coefficient $R^2$ as an indicator of the dependency of the NOx current Ip2 on the oxygen concentration was calculated from results of the model gas measurement at the end of the diesel engine durability test, and, based on a value thereof, a degree of decomposition of NOx in the inner pump electrode 22 was determined.

The main pump current density, the main pump current Ip0, the (total) area of the inner pump electrode 22, a result of determination on whether the NOx sensitivity change rate is preferable (DETERMINATION 1), and a result of determination on whether the degree of decomposition of NOx is preferable (DETERMINATION 2) of each of the gas sensors of Example 1, Examples 6 to 10, and Conventional Example 6 are shown in Table 2 as a list.

TABLE 2

| LEVEL | DENSITY OF CURRENT FLOWING THROUGH MAIN PUMP CELL [mA/mm$^2$] | Ip0 [mA] | AREA [mm$^2$] | DETERMINATION 1 | DETERMINATION 2 |
|---|---|---|---|---|---|
| EXAMPLE 1 | 0.40 | 3.0 | 7.5 | ○ | ○ |
| EXAMPLE 6 | 0.33 | 2.5 | 7.5 | ○ | ○ |
| EXAMPLE 7 | 0.53 | 4.0 | 7.5 | ○ | Δ |
| EXAMPLE 8 | 0.30 | 3.0 | 10.0 | ○ | ○ |
| EXAMPLE 9 | 0.40 | 4.0 | 10.0 | ○ | ○ |
| EXAMPLE 10 | 0.27 | 4.0 | 15.0 | ○ | ○ |
| CONVENTIONAL EXAMPLE 6 | 0.27 | 4.0 | 15.0 | Δ | ○ |

In determination on the NOx sensitivity change rate of each of the gas sensors 100 shown as DETERMINATION 1, in a case where the absolute value of the NOx sensitivity change rate is 10% or less, it is determined that the change in NOx sensitivity is desirably suppressed, and a circle is marked in Table 2.

In a case where the absolute value of the NOx sensitivity change rate is more than 10% and 20% or less, it is determined that the change in NOx sensitivity is suppressed within a range allowable in actual use of each of the gas sensors 100, and a triangle is marked in Table 2.

On the other hand, in determination on the degree of decomposition of NOx shown as DETERMINATION 2, in a case where the value of the determination coefficient $R^2$ is 0.975 or more, it is determined that decomposition of NOx is desirably suppressed, and a circle is marked in Table 2.

In a case where the value of the determination coefficient $R^2$ is 0.950 or more and less than 0.975, it is determined that decomposition of NOx is suppressed within a range allowable in actual use of each of the gas sensors 100, and a triangle is marked in Table 2.

In Table 2, the circle is marked for each of the gas sensors 100 of Example 1 and Examples 6 to 10 in DETERMINATION 1, and the circle is marked for each of the gas sensors 100 other than the gas sensor 100 of Example 7 for which the triangle is marked in DETERMINATION 2.

On the other hand, for the gas sensor 100 of Conventional Example 6, the triangle is marked in DETERMINATION 1 while the circle is marked in DETERMINATION 2.

The above-mentioned results indicate that, in a case where the inner pump electrode 22 is provided in the first internal space 20, the change in NOx sensitivity is smaller in the configuration in which the inner pump electrode 22 is provided only on the lower surface of the second solid electrolyte layer 6 or the configuration in which the inner pump electrode 22 provided on the lower surface of the second solid electrolyte layer 6 extends to the side surfaces of the first internal space 20 as the spacer layer 5 than in the configuration in which the inner pump electrode 22 is provided on both of the lower surface of the second solid electrolyte layer 6 and the upper surface of the first solid electrolyte layer 4.

The results further indicate that use of the configuration in which the main pump cell current density is 0.4 mA/mm$^2$ or less is preferable to prevent decomposition of NOx in a case where the measurement gas has a high oxygen concentration.

(Evaluation 3: Evaluation of Influence of Form of Second Diffusion Control Part)

The influence of a difference in form of the second diffusion control part 13 on the NOx sensitivity change rate was evaluated. Specifically, five types of gas sensors 100 having different diffusion resistance ratios D1/D2 between the upper slit 13a and the lower slit 13b including the gas sensor 100 of Example 1 in Evaluation 1 (Example 1 and Examples 11 to 14) were manufactured, and the gas sensor 100 in which the second diffusion control part 13 did not include the upper slit 13a illustrated in FIGS. 4A and 4B was manufactured (Example 15).

In the gas sensors 100 of Examples 11, 12, 13, and 14, diffusion resistance ratios D1/D2 were respectively 1.2, 1.5, 2.0, and 5.0 as the upper slit 13a and the lower slit 13b had different gaps, while the gas sensors 100 each had the configuration in which the main pump cell current density was 0.4 mA/mm$^2$ as in the gas sensor 100 of Example 1. Specifically, the upper slit 13a had a different thickness from that of Example 1 while the lower slit 13b had the same thickness as that of Example 1. The other configuration was the same as that of Example 1.

The gas sensor 100 of Example 15 had a configuration in which the upper slit 13a was not provided, and the lower slit 13b was formed to have a width of 2000 μm and a gap of 15 μm while having the configuration in which the main pump cell current density was 0.4 mA/mm$^2$ as in the gas sensor 100 of Example 1.

The diesel engine durability test was conducted on each of the gas sensors 100 to evaluate the NOx sensitivity change rate as in Evaluation 2.

The main pump current density, the diffusion resistance ratio D1/D2, and the NOx sensitivity change rate of each of the gas sensors of Example 1 and Examples 11 to 15 are shown in Table 3 as a list. As for the gas sensor of Example 15 in which the upper slit 13a is not provided, the upper slit 13a can be considered to have infinite diffusion resistance D1, so that the diffusion resistance ratio D1/D2 is shown to be infinite.

TABLE 3

| LEVEL | DENSITY OF CURRENT FLOWING THROUGH MAIN PUMP CELL [mA/mm$^2$] | DIFFUSION RESISTANCE RATIO D1/D2 | NOx SENSITIVITY CHANGE RATE [%] |
|---|---|---|---|
| EXAMPLE 1 | 0.40 | 1.0 | −8.0 |
| EXAMPLE 11 | 0.40 | 1.2 | −7.6 |
| EXAMPLE 12 | 0.40 | 1.5 | −6.9 |
| EXAMPLE 13 | 0.40 | 2.0 | −6.2 |
| EXAMPLE 14 | 0.40 | 5.0 | −5.3 |
| EXAMPLE 15 | 0.40 | (∞) | −4.0 |

It can be seen from Table 3 that the absolute value of the NOx sensitivity change rate tends to decrease with increasing value of the diffusion resistance ratio D1/D2 in the gas sensors including the gas sensor of Example 15. The results indicate that an increase in diffusion resistance ratio D1/D2 is effective in suppression of the change in NOx sensitivity over time.

While the invention has been shown and described in detail, the foregoing description is in all aspects illustrative and not restrictive. It is therefore understood that numerous modifications and variations can be devised without departing from the scope of the invention.

What is claimed is:

1. A sensor element for a limiting-current type gas sensor measuring concentration of NOx in a measurement gas, said sensor element having a base part made of an oxygen-ion conductive solid electrolyte, said sensor element comprising:
   a gas inlet through which said measurement gas is introduced from an external space;
   a first internal space communicating with said gas inlet under predetermined diffusion resistance;
   a first diffusion control part being located closest to said gas inlet;
   a second diffusion control part composed of a pair of slits including a first slit and a second slit, each communicating with said first internal space, and located between said first diffusion control part and said first internal space;
   a main pump cell as an electrochemical pump cell including an inner pump electrode located to face said first internal space, an out-of-space pump electrode located to face a space other than said first internal space, and said solid electrolyte located between said inner pump electrode and said out-of-space pump electrode;
   a measurement electrode located inside said sensor element, a third diffusion control part being located between said measurement electrode and said first internal space;
   a reference electrode located inside said sensor element and capable of being in contact with a reference gas;
   a measurement pump cell as an electrochemical pump cell including said measurement electrode, said out-of-space pump electrode, and said solid electrolyte located between said measurement electrode and said out-of-space pump electrode; and
   a heater part buried in said sensor element and heating said sensor element, wherein
   said inner pump electrode is at least made of a cermet of a Pt—Au alloy and zirconia,
   said inner pump electrode is located, from among surfaces defining said first internal space, at least on a surface farthest from said heater part in a thickness direction of said sensor element, and is not located on a surface closest to said heater part in said thickness direction, and
   a diffusion resistance at the first slit of said pair of slits, which is farther from said heater part in said thickness direction, is higher than the diffusion resistance at the second slit of said pair of slits, which is closer to said heater part in said thickness direction.

2. The sensor element according to claim 1, wherein
   a current flowing through said main pump cell when said sensor element is driven under a gas atmosphere having an oxygen concentration of 18% and the balance being nitrogen has a current density of 0.4 mA/mm$^2$ or less.

3. The sensor element according to claim 2, wherein
   said inner pump electrode extends to, from among said surfaces defining said first internal space, a surface along a longitudinal direction and said thickness direction of said sensor element.

4. The sensor element according to claim 2 further comprising:
   a second internal space communicating with said first internal space under predetermined diffusion resistance; and
   an auxiliary pump cell as an electrochemical pump cell including an auxiliary pump electrode located to face said second internal space, said out-of-space pump electrode, and said solid electrolyte located between said auxiliary pump electrode and said out-of-space pump electrode, wherein
   said measurement electrode is provided so that said third diffusion control part is located at least between said measurement electrode and said second internal space.

5. The sensor element according to claim 1, wherein
   said inner pump electrode extends to, from among said surfaces defining said first internal space, a surface along a longitudinal direction and said thickness direction of said sensor element.

6. The sensor element according to claim 1 further comprising:
   a second internal space communicating with said first internal space under predetermined diffusion resistance; and
   an auxiliary pump cell as an electrochemical pump cell including an auxiliary pump electrode located to face said second internal space, said out-of-space pump electrode, and said solid electrolyte located between said auxiliary pump electrode and said out-of-space pump electrode, wherein
   said measurement electrode is provided so that said third diffusion control part is located at least between said measurement electrode and said second internal space.

7. A sensor element for a limiting-current type gas sensor measuring concentration of NOx in a measurement gas, said sensor element having a base part made of an oxygen-ion conductive solid electrolyte, said sensor element comprising:
   a gas inlet through which said measurement gas is introduced from an external space;
   a first internal space communicating with said gas inlet under predetermined diffusion resistance;
   a first diffusion control part being located closest to said gas inlet;
   a second diffusion control part composed of a pair of slits including a first slit and a second slit, each communicating with said first internal space, and located between said first diffusion control part and said first internal space;

a main pump cell as an electrochemical pump cell including an inner pump electrode located to face said first internal space, an out-of-space pump electrode located to face a space other than said first internal space, and said solid electrolyte located between said inner pump electrode and said out-of-space pump electrode;

a measurement electrode located inside said sensor element, a third diffusion control part being located between said measurement electrode and said first internal space;

a reference electrode located inside said sensor element and capable of being in contact with a reference gas;

a measurement pump cell as an electrochemical pump cell including said measurement electrode, said out-of-space pump electrode, and said solid electrolyte located between said measurement electrode and said out-of-space pump electrode; and a heater part buried in said sensor element and heating said sensor element, wherein said inner pump electrode is at least made of a cermet of a Pt—Au alloy and zirconia, said inner pump electrode is not located between said heater part and said first internal space at least in a thickness direction of said sensor element, and a diffusion resistance at the first slit of said pair of slits, which is farther from said heater part in said thickness direction, is higher than the diffusion resistance at the second slit of said pair of slits, which is closer to said heater part in said thickness direction.

8. The sensor element according to claim 7, wherein a current flowing through said main pump cell when said sensor element is driven under a gas atmosphere having an oxygen concentration of 18% and the balance being nitrogen has a current density of 0.4 mA/mm$^2$ or less.

9. The sensor element according to claim 8, wherein said inner pump electrode extends to, from among surfaces defining said first internal space, a surface along a longitudinal direction and said thickness direction of said sensor element.

10. The sensor element according to claim 8 further comprising:

a second internal space communicating with said first internal space under predetermined diffusion resistance; and an auxiliary pump cell as an electrochemical pump cell including an auxiliary pump electrode located to face said second internal space, said out-of-space pump electrode, and said solid electrolyte located between said auxiliary pump electrode and said out-of-space pump electrode, wherein said measurement electrode is provided so that said third diffusion control part is located at least between said measurement electrode and said second internal space.

11. The sensor element according to claim 7, wherein said inner pump electrode extends to, from among surfaces defining said first internal space, a surface along a longitudinal direction and said thickness direction of said sensor element.

12. The sensor element according to claim 7 further comprising:

a second internal space communicating with said first internal space under predetermined diffusion resistance; and an auxiliary pump cell as an electrochemical pump cell including an auxiliary pump electrode located to face said second internal space, said out-of-space pump electrode, and said solid electrolyte located between said auxiliary pump electrode and said out-of-space pump electrode, wherein said measurement electrode is provided so that said third diffusion control part is located at least between said measurement electrode and said second internal space.

* * * * *